United States Patent [19]

Vité

[11] Patent Number: 4,839,383

[45] Date of Patent: Jun. 13, 1989

[54] COMPOSITIONS FOR COMBATTING BARK BEETLES

[75] Inventor: Jean Pierre Vité, Freiburg, Fed. Rep. of Germany

[73] Assignee: Celamerck GmbH & Co., Ingelheim am Rhein, Fed. Rep. of Germany

[21] Appl. No.: 90,524

[22] Filed: Aug. 28, 1987

Related U.S. Application Data

[63] Continuation of Ser. No. 925,892, Oct. 31, 1986, abandoned, which is a continuation of Ser. No. 806,741, Dec. 9, 1985, abandoned.

[30] Foreign Application Priority Data

Dec. 10, 1984 [DE] Fed. Rep. of Germany ....... 3444976

[51] Int. Cl.$^4$ ...................... A01N 35/00; A01N 43/16
[52] U.S. Cl. .................................. 514/456; 424/84; 514/691; 514/919
[58] Field of Search ................. 424/84; 514/919, 456, 514/691

[56] References Cited

U.S. PATENT DOCUMENTS

| | | | |
|---|---|---|---|
| 3,755,563 | 8/1973 | Vité | 424/84 |
| 4,299,818 | 11/1981 | Vité et al. | 424/84 |
| 4,474,755 | 10/1984 | Neal, Jr. et al. | 424/84 |

FOREIGN PATENT DOCUMENTS

| | | | |
|---|---|---|---|
| 2832248 | 1/1980 | Fed. Rep. of Germany | 424/84 |
| 41040 | 12/1971 | Japan | 424/84 |
| 0030905 | 3/1981 | Japan | 424/84 |
| 0179101 | 11/1982 | Japan | 514/919 |

*Primary Examiner*—Leonard Schenkman
*Attorney, Agent, or Firm*—Felfe & Lynch

[57] ABSTRACT

A composition for combatting bark beetles, particularly of the Dendroctonus genera, containing mixtures of pheromone components having a repelling or attracting effect.

6 Claims, No Drawings

COMPOSITIONS FOR COMBATTING BARK BEETLES

This is a continuation of copending application Ser. No. 925,892, filed Oct. 31, 1986, now abandoned, which, in turn, is a continuation of application Ser. No. 806,741, filed Dec. 9, 1985, now abandoned.

This invention relates to attractant and repellant compositions for combatting bark beetles and to methods of using these compositions.

BACKGROUND OF THE INVENTION

It is known that numerous genera of bark beetles control the infestation of their host trees by giving off sex-specific pheromones [J.A.A. Renwick and J.P. Vité, Contrib. Boyce Thompson Inst. 24 (1970) 283].

The females of the Southern pine beetle *Dendroctonus frontalis* give off the bicylic ketal frontaline (1,5-dimethyl-6,8-dioxabicyclo[3.2.1]octane) of the formula

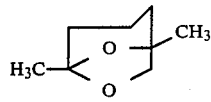
(I)

(I) as an aggregation pheromone, attract other male and female beetles of this genus and thus bring about a mass attack on the host tree. The attraction is synergistically intensified by the terpene alcohol trans-verbenol (trans-4,6,6-trimethylbicyclo-[3.1.1]hept-3-en-2-ol) of the formula

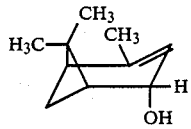
(II)

and/or the monoterpene α-pinene of the formula

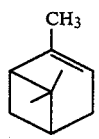
(III)

(III). Mixtures of (I) with (II) or (III) are used under the name "FRONTALURE" and are prior art.

It is also known that the female beetles of the genus *Dendroctonus ponderosae* give off trans-verbenol (II) as an aggregation pheromone which together with terpenes attracts both sexes but predominantly males of the species (G.B. Pitman and J.P. Vité; Can. Entomol., 101 (1969) 143).

Mixtures of (II) with (III) and/or myrcene of the formula

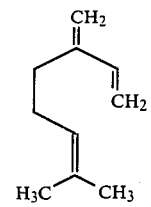
(IX)

are used as attractants under the name "PONDE-LURE" and are prior art. The males of *D. ponderosae* give off exo-brevicomine (7-ethyl-5-methyl-6,8-diocabicyclo[3.2.1]octane) of the formula

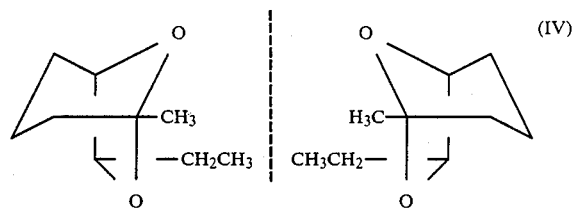
(IV)

(+)-exo-brevicomine (1R) (−)-exo-brevicomine (1S), endo-brevicomine (endo-7-ethyl-5-methyl-6,8-dioxabicyclo[3.2.1]octane]of the formula

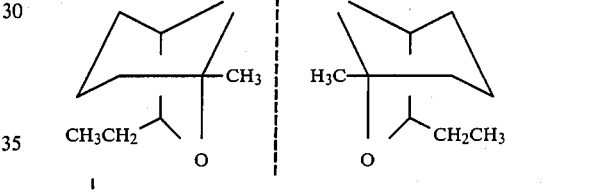
(VI)

(+)-endo-brevicomine (1R) (−)-endo-brevicomine (1S), and frontaline (I). Racemic exo-brevicomine (IV), endo-brevicomine (VI) and frontaline (I) reduce the catching power of the "PONDELURE" mixture (L.C. Ryker and L.M. Libbey; Chem. Ecolog. 8 (1982) 1399).

The infestation of the host trees is thus controlled by the interaction of female specific pheromone components such as frontaline (I) and trans-verbenol (II), and male-specific components such as exo-brevicomine (IV), endo-brevicomine (VI) and verbenone (4,6,6-trimethyl-bicyclo[3.2.1]hept-3-en-2-one) of the formula

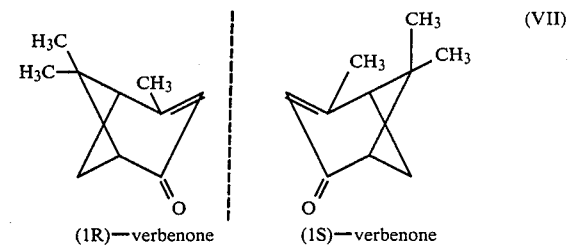
(VII)

(1R)—verbenone    (1S)—verbenone

DESCRIPTION OF THE INVENTION

More particularly, the present invention relates to compositions for combatting bark beetles in which the behavior of the bark beetles is influenced by female-specific or malespecific pheromones or by combinations of the two, especially compositions for combatting bark beetles containing at least one of the following compounds (a) optically active verbenone (VII), racemic or optically active exo-brevicomine (IV), racemic or optically active endo-brevicomine (VI), and, if desired, one or more of the following compounds
(b) frontaline (I), α-pinene (III), trans-verbenol (II), dipentene of the formula $$\text{(VIII)}$$

myrcene (IX), and terpinolene [1-methyl-4-(1-methyl-4-(1-methyl-ethanyliden)cyclohexene]of the formula $$\text{(V)}$$

By making different combinations of the above-mentioned pheromone components it is possible to produce bouquets of scents which either have an attracting effect or an inhibiting effect. Optically active components may occur in pure or in enriched form. In some cases it is sufficient to use the racemate since the inhibiting effect of one enantiomer will predominate over the attracting effect of the optical antipodes present in the same proportion.

The attracting effect of the combination according to the present invention is determined by the use of (+)-endobrevicomine (VI), (+)-exo-brevicomine (IV) and (+)-verbenone (VIII), while the inhibiting effect can be achieved both with the racemic compounds (IV) and (VI), and also with (−)-endobrevicomine (VI), (−)-exo-brevicomine (IV) and (−)-verbenone (VII).

The compositions according to the present invention are suitable for combatting Dendroctonus genera, particularly *Dendroctonus frontalis* and *Dendroctonus ponderosae*.

Mixtures of (+)-endo-brevicomine (VI) and/or (+)-exo-brevicomine (IV) and/or (+)-verbenone (VII) as male-specific attractants with frontaline (I) and/or trans-verbenol (II) as predominantly female-specific attractants and, if desired, other additives consisting of α-pinene (III) and/or myrcene (IX) and/or methylbutanol and/or terpinolene (V) have an attractant effect, for example.

An inhibiting effect is exerted by (−)-verbenone (VII), (−)-exo-brevicomine (IV), or (−)-endo-brevicomine (VI), either as pure substances or in admixture, while the repellent effect of the (−)-enantiomer in the case of the two brevicomines is so marked that racemic exo-brevicomine (IV) and racemic endobrevicomine (VI) can also have a repellent effect.

Due to the high genus-specificity of the bouquet of the fragrances, a special mixture is required according to the genus of the beetle which is to be controlled.

For the inhibiting effect, the male-specific pheromones can be used in combination with the female-specific pheromones, optionally together with compounds simulating tree scent.

A particularly useful combination of (+)-endobrevicomine (VI) with frontaline (I) to which optionally trans-verbenole (II), alpha-pine (IV) and/or terpinolene (V) may be added, should be emphasized. This mixture has a good attracting effect on D. frontalis.

A further particularly useful material is (−)-verbenone (VII) and/or (−)-endo-brevicomine (VI), optionally in combination with dipentene (VIII). This effects a good inhibiting action toward D. frontalis.

It can be shown that (−)-verbenone (VII) itself has very good inhibiting activity in repelling D. frontalis. (−)-verbenone may therefore be applied in dispensing systems useful for this purpose. It is preferred to spray microencapsulated verbenone or a mixture of verbenone and a carrier comprising a solution of a polymer in an organic solvent or a suspension of a polymer in water, which polymer acts as retarding agent. Such formulations can be sprayed by hand pumps or by airplanes.

Compositions according to the present invention with an inhibiting or attracting effect may be used either on their own or in combination: in the mass attacks of Dendroctonus genera which are widespread in North America, large areas of forest are damaged. The centers of attack may extend over many acres. The beetles are generally combatted by removing any affected trees or by arranging a "buffer strip," i.e. by felling healthy areas of forest around the center of the attack, whereby a treeless aisle is formed which is wide enough to prevent the pest from jumping across.

The bark beetles remain confined to the original area of the attack or are taken out of the forest with the felled trees. Using a composition according to the present invention, it is possible to back up this method of control: compositions with an attracting activity are applied in the area already attacked, fix the pest and prevent its propagation. Compositions with an inhibiting effect are applied around the edge of the site, i.e. to prevent further propagation of the pest. The inhibiting compositions may also be used by themselves to confine the bark beetles.

Moreover, compositions with an inhibiting effect may be used for preventively protecting trees, preferably in gardens and parks.

Compositions with an attracting effect may also be used in a manner known per se for catching the beetles en masse or for monitoring the pest population.

The pheromone mixture may be applied by methods known per se, while specific formulations can be used to build up a long-term effect, lasting not less than two weeks.

The pheromone mixtures may be applied using dispensers. such as those known from German Offenlegungsschrift Nos. 28 32 248 and 29 46 655.

When combatting bark beetles in forested areas which are difficult to reach, the active substance may be applied from an airplane or by means of portable spray pumps directly at the site.

The pheromone mixture may be sprayed in the form of microencapsulated preparations or together with a polymer, such as ethyl cellulose, polyacrylate, polyvinyl pyrrolidone or polyester, dissolved in an organic solvent as a formulation with delayed release of the active substance.

The male-specific brevicomines (IV, VI) and verbenone (VII) may occur in enantiomeric forms, the attracting activity coming from the (+)-enantiomer, while the inhibiting activity comes from the (−)-enantiomer. The association of the (+) and (−)-enantiomers to give the absolute configuration according to Kahn Ingold and Prelog, as shown above, corresponds to the present state of scientific literature.

The arrangement of the absolute configuration is not yet known in the case of verbenone (VII).

The differentiation of the pheromone activity in the (+) and (−)-isomers achieved according to the present invention relates to the rotational values measured for the optically active compounds IV, VI and VII. Compounds of the formula IV, VI and VII with an optical purity of ee greater than 25% are regarded as optically active.

The following examples illustrate the present invention and will enable others skilled in the art to understand it more completely. It should be understood, however, that the invention is not limited solely to the particular examples given below.

EXAMPLE 1

Flight of *D. frontalis* into funnel traps

Test site: Texas

| Lure | n | ♂:♀ |
|---|---|---|
| Frontalure[1] + Terpene[2] (= "A") | 45 | 3.1:1 |
| A and (+)-endo-brevicomine[3] ((+) − VI) | 346 | 2.2:1 |
| A and (−)-endo-brevicomine[3] ((−) − VI) | 6 | 1:1 |
| A and (−)-verbenone ((−) − VII) | 12 | 3.0:1 |
| A and racemic verbenone (VIII) | 12 | 1.4:1 |
| Terpenes[2] | 1 | 0:1 |

[1]Frontaline (I) in α-pinene (III) 1:2 (1 mg/hr).
[2]Sponge containing 80 ml of pine turpentine (approx. 150 mg/hr).
The pine turpentine was added to imitate the scent of the host tree.
[3]Capillary 2 mg (= 100 mcg/day).

EXAMPLE 2

Inhibiting effect of (−)-verbenone (VII) in a test in open land

The comparative test was carried out on two sites in a ten-year-old group of pines in Texas attacked by *D. frontalis* which had been monitored since June 19, 1985.

Two sites of attack were selected. In site No. 1, used as an untreated control, the attack by bark beetles proceeded normally; site No. 2 was treated with (−)-verbenone (VII).

The sites were checked before the treatment (August 2), on the day of the treatment (August 7) and 14 days after the treatment (August 21).

To characterize the density of trees in the areas under investigation the "pine basal area" (PBA) was used. The pine basal area is determined by determining the ratio of the total surface area of the trunk cross section to the total surface area of the stand of trees under investigation (sq. ft/acre).

Site No. 1 was less densely populated with trees, having a PBA of 75.1 (sq.ft/acre), than site No. 2 with a PBA of 154.7 (sq.ft/acre). It is known that, with a high density of trees, sites affected by *D. frontalis* spread particularly quickly on account of the high pressure of population and the smaller distance between the trees. The comparison tests investigating the inhibition of the sites of the bark beetles was expected to show that site No. 2 is subject to a greater population pressure than untreated site No. 1 used as a comparison.

In site No. 2, 146 trees standing in the immediate vicinity of the trees already attacked ("buffer strip") were treated from the soil with a mixture of (−)-verbenone (VII) and a polymer with a delayed release of active substance.

The quantity applied was 6.5 g of (−)-verbenone per tree. The sprayable solution was prepared as follows: (−)-verbenone (e.e. 50%) were mixed with a liquid polymeric microencapsulator in proportions of 1:20 (i.e. 1 ltr. of verbenone to 20 ltr. polymer).

The test results are shown in the following table:

| | Site No. 1 | Site No. 2 |
|---|---|---|
| Before treatment (August 7, 1985) | | |
| Pine basal area (sq. ft./acre) | 75.1 | 154.7 |
| Number of pines attacked | 136 | 103 |
| Number of pines newly attacked between August 2 and August 7 | 10 | 14 |
| Attack rate (pines per day) from August 2 to 7 | 1.7 | 2.3 |
| After treatment (August 21, 1985) | | |
| Number of pines newly attacked between August 7 and 21 | 22 | 6 |
| Rate of attack (pines per day) from August 7 to 21 | 1.6 | 0.4 |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. A method of controlling an infestation of trees by bark beetles of the dendroctonus genera, which comprises applying to at least one of said trees an effective repellent amount of a compound selected from the group consisting of (−)-verbenone, (−)-exo-brevicomine and (−)-endo-brevicomine.

2. The method of claim 1, wherein said compound is applied in combination with dipentene.

3. A method of controlling an infestation of trees in a site by bark beetles of the dendroctonus genera, which comprises applying around said site an effective repellent amount of a compound selected from the group consisting of (−)-verbenone, (−)-exo-brevicomine and (−)-endo-brevicomine.

4. The method of claim 3, wherein said compound is applied in combination with dipentene.

5. A method of controlling an infestation of trees in a site by bark beetles of the dendroctonus genera, which comprises applying around said site an effective repellent amount of a compound selected from the group consisting of (−)-verbenone, (−)-exo-brevicomine and (−)-endo-brevicomine, and applying to an area within said site an effective attractant amount of at least one compound selected from the group consisting of (+)-verbenone, (+)-exo-brevicomine and (+)-endo-brevicomine, and at least one compound selected from the group consisting of frontaline, trans-verbenol, alphapinene, myrcene and terpinolene.

6. A method of claim 5, which comprises applying around said site an effective repellent amount of a compound selected from the group consisting of (−)-verbenone, (−)-exo-brevicomine and (−)-endo-brevicomine, in combination with dipentene, and applying to an area within said site an effective attractant amount of at least one compound selected from the group consisting of (+)-verbenone, (+)-exo-brevicomine and (+)-endo-brevicomine, and at least one compound selected from the group consisting of frontaline, trans-verbenol, alpha-pinene, myrcene and terpinolene.

* * * * *